US00PP22915P2

(12) United States Plant Patent
Egger

(10) Patent No.: US PP22,915 P2
(45) Date of Patent: Jul. 31, 2012

(54) ***KNIPHOFIA* PLANT NAMED 'PAPAYA POPSICLE'**

(50) Latin Name: ***Kniphofia* spp.**
Varietal Denomination: Papaya Popsicle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/066,135

(22) Filed: Apr. 6, 2011

(51) Int. Cl.
*A01H 5/00* (2006.01)

(52) U.S. Cl. ..... Plt./443

(58) Field of Classification Search ..... Plt./443
See application file for complete search history.

*Primary Examiner* — Annette Para

(74) *Attorney, Agent, or Firm* — Klarquist Sparkman, LLP

(57) ABSTRACT

A new and distinct *Kniphofia* plant characterized by its very early blooming, repeat blooming, compact habit with multiple crowns, narrow, grassy leaves, red orange flowers, and excellent vigor.

1 Drawing Sheet

Botanical denomination: *Kniphofia* spp.
Cultivar designation: 'Papaya Popsicle'.

BACKGROUND OF THE INVENTION

The present invention relates to a new and distinct *Kniphofia*, and given the cultivar name is 'Papaya Popsicle'. *Kniphofia* is in the family Asphodelaceae. 'Papaya Popsicle' is a hybrid resulting from a planned breeding program to produce compact, reblooming *Kniphofia*. The cross was made using the following proprietary, unreleased plants: *Kniphofia* 10-1, as the seed parent, and *Kniphofia* 10-2, as the pollen parent. It was selected for best habit, flower color, reblooming, and crown count from many seedlings of the cross in Canby, Oreg.

Compared to *Kniphofia* 'Bressingham Comet' (an unpatented plant), the seed parent, the new cultivar is more free flowering with red orange flowers rather than a bicolor with yellow to red orange flowers.

Compared to its sibling, *Kniphofia* 'Mango Popsicle' (Plant patent application Ser. No. 13/066,147), the new cultivar is shorter with red orange flowers rather than yellow orange.

SUMMARY OF THE INVENTION

The new cultivar is unique and characterized by:

1. very early blooming (flowers the first year in 30 cell plugs)
2. repeat blooming from May through September in Canby, Oreg.
3. compact habit with multiple crowns
4. narrow, grassy leaves
5. red orange flowers
6. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a plant of a one-year-old *Kniphofia* 'Papaya Popsicle' in the ground in the trial field in July in Canby, Oreg.

DETAILED PLANT DESCRIPTION

The following is a detailed description of the new *Kniphofia* cultivar based on observations 32 cell size, six-month-old specimens grown from tissue culture, grown outside in part sun in Canby, Oreg. The color descriptions are all based on The Royal Horticultural Society Colour Chart, 5$^{th}$ edition.

Plant:
- *Type*.—Rhizomatous herbaceous perennial.
- *Hardiness*.—USDA Zones 6 to 9.
- *Size*.—Grows to 32 cm wide and 44 cm tall from the top of the soil to the top of the foliage.
- *Crown #*.—5 to 9.
- *Form*.—Upright and clumping.

Leaf:
- *Type*.—Simple.
- *Shape*.—Strap-like.
- *Arrangement*.—Basal rosette.
- *Blade size*.—Grows to 44 cm long and 10 mm wide.
- *Margins*.—Entire.
- *Apex*.—Acuminate.
- *Base*.—Clasping.
- *Surface texture*.—Glabrous on both surfaces.
- *Venation*.—Parallel.
- *Color*.—Top and bottom side Green 137A.

Inflorescence:
- *Type*.—Spike-like scapose raceme.
- *Number of flowers per raceme*.—About 100.
- *Inflorescence*.—14 cm long and 6 cm wide.
- *Peduncle description*.—Grows to 37 cm long and 6 mm wide, glabrous, Yellow Green 152A.

*Pedicle description.*—5 mm long, glabrous, Greyed Orange 165A.

*Bloom time*.—June through September in Canby, Oreg.

*Lastingness*.—An inflorescence lasts for 2 to 4 weeks depending on the temperatures.

Flower bud:

*Size.*—27 mm long and 5 mm wide.

*Shape*.—Cylindrical.

*Surface texture*.—Glabrous.

*Color*.—Orange 34A, Greyed Yellow 160B on bottom at base.

Flower:

*Type*.—Actinomorphic.

*Shape*.—Cylindrical and tubular.

*Size*.—Grows to 27 mm deep and 9 mm wide.

*Texture*.—Waxy.

*Surface texture*.—Glabrous inside and outside.

*Color*.—Inside and out: Orange Red 34A with Green Yellow 1C on end nearest the stem on the underside.

*Corolla description.*—6 lobed fused tepals, 27 mm long and 9 mm wide, tube 25 mm long and 5 mm wide, lobes reflex, each 3 mm wide and 3 mm long, ovate, entire, obtuse to acute, inside and out: Orange Red 34A with Green Yellow 1C on end nearest the stem on the underside.

*Pistil description*.—One, 22 mm long, ovary 2 mm long 1.5 mm wide, Yellow Green 144A, style 19 mm long, Red Orange 31D, stigma White NN155A.

*Stamen.*—6, 26 mm long, filaments 25 mm long, and White NN155A, anthers 1 mm long and Yellow 10A, pollen Yellow 10A.

*Fragrance*.—None.

Fruit and seed.—None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

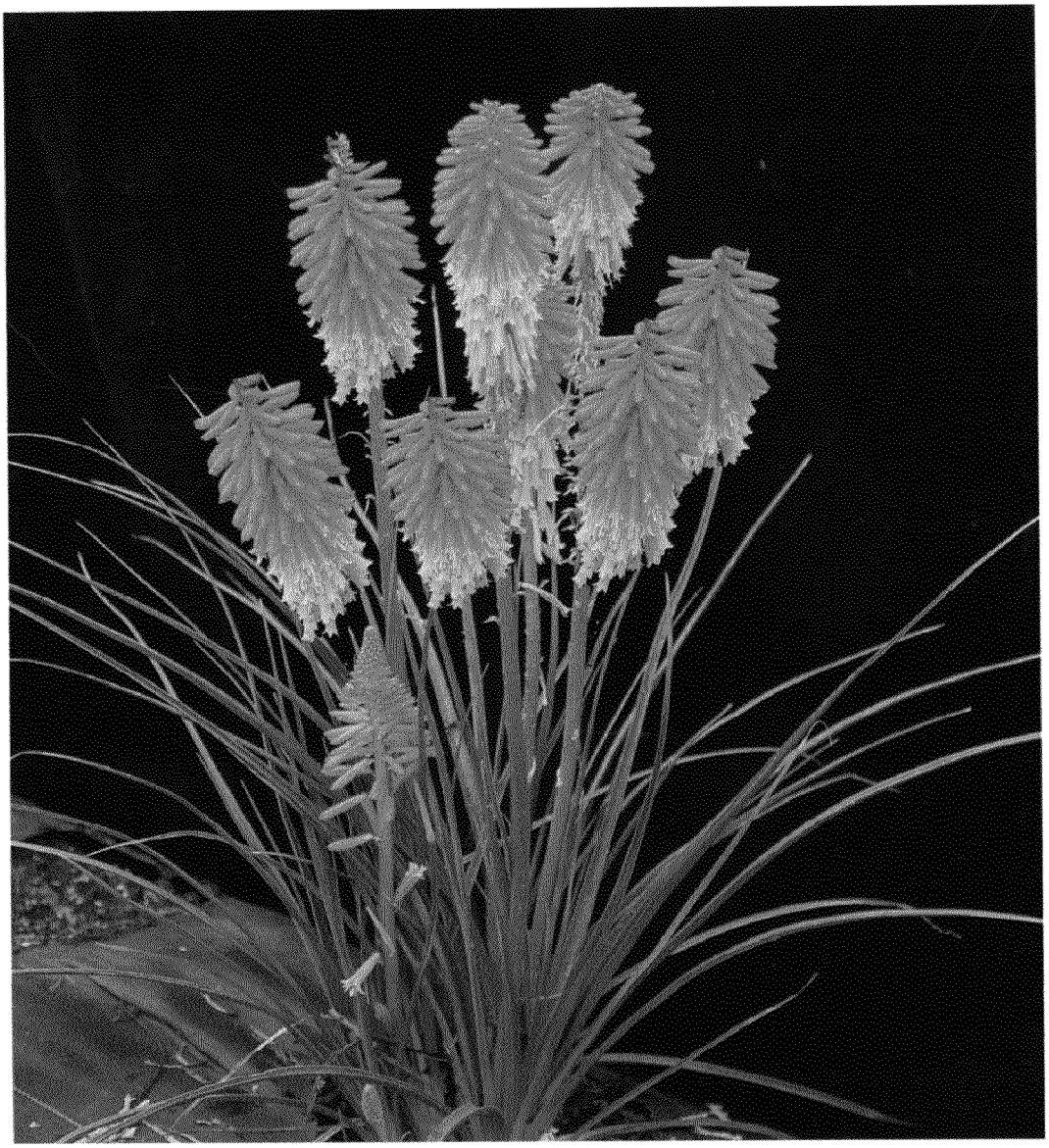

* * * * *